(12) United States Patent
Hopkins

(10) Patent No.: US 12,102,366 B2
(45) Date of Patent: Oct. 1, 2024

(54) POLY-AXIAL FIXATION POSTS

(71) Applicant: Zimmer, Inc., Warsaw, IN (US)

(72) Inventor: Andrew Rolfe Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 10 days.

(21) Appl. No.: 17/939,513

(22) Filed: Sep. 7, 2022

(65) Prior Publication Data

US 2022/0409253 A1    Dec. 29, 2022

Related U.S. Application Data

(60) Continuation of application No. 16/773,752, filed on Jan. 27, 2020, now Pat. No. 11,464,555, which is a
(Continued)

(51) Int. Cl.
*A61B 17/86* (2006.01)
*A61B 17/84* (2006.01)
(Continued)

(52) U.S. Cl.
CPC ........ *A61B 17/8605* (2013.01); *A61B 17/846* (2013.01); *A61F 2/4081* (2013.01);
(Continued)

(58) Field of Classification Search
CPC .............. A61B 17/8605; A61B 17/846; A61B 17/8685
See application file for complete search history.

(56) References Cited

U.S. PATENT DOCUMENTS 4,944,759 A    7/1990    Mallory et al.
5,360,448 A    11/1994   Thramann
(Continued)

FOREIGN PATENT DOCUMENTS

CN    103209651 A    7/2013
CN    103702627 A    4/2014
(Continued)

OTHER PUBLICATIONS

U.S. Appl. No. 15/862,931, now U.S. Pat. No. 10,595,916, filed Jan. 5, 2018, Poly-Axial Fixation Posts.
(Continued)

*Primary Examiner* — Olivia C Chang
(74) *Attorney, Agent, or Firm* — Schwegman Lundberg & Woessner, P.A.

(57) ABSTRACT

This disclosure includes apparatus and methods to attach an orthopedic device to a bone. The method can comprise locating a baseplate on a glenoid of a patient, the base plate including at least a first fastener bore, creating a first post hole in the glenoid for locating a first fixation post, the first fixation post including a quasi-spherical head and a porous metal sleeve, and driving the first fixation post through the first fastener bore and into the first post hole. The porous metal sleeve can engage the first post hole and the quasi-spherical head can contact at least the first wall of the first fastener bore to removeably lock the quasi-spherical head to the baseplate. Driving the first fixation post can create an initial compression between the baseplate and the glenoid. The porous metal sleeve can receive bone ingrowth to maintain the initial compression.

19 Claims, 7 Drawing Sheets

Related U.S. Application Data division of application No. 15/862,931, filed on Jan. 5, 2018, now Pat. No. 10,595,916.

(60) Provisional application No. 62/444,148, filed on Jan. 9, 2017.

(51) Int. Cl.
*A61F 2/40* (2006.01)
*A61F 2/30* (2006.01)

(52) U.S. Cl.
CPC ... *A61B 17/8625* (2013.01); *A61B 2017/8655* (2013.01); *A61F 2002/30245* (2013.01); *A61F 2002/30329* (2013.01); *A61F 2002/30919* (2013.01)

(56) References Cited

U.S. PATENT DOCUMENTS

| | | | |
|---|---|---|---|
| 6,095,817 | A | 8/2000 | Wagner et al. |
| 7,909,883 | B2 | 3/2011 | Sidebotham |
| 8,075,312 | B2 | 12/2011 | Collins et al. |
| 8,221,479 | B2 | 7/2012 | Glazer et al. |
| 8,424,183 | B2 | 4/2013 | Thomas |
| 8,562,348 | B2 | 10/2013 | Collins et al. |
| 8,574,273 | B2 | 11/2013 | Russell et al. |
| 8,623,093 | B2 | 1/2014 | Dickerson |
| 8,899,982 | B2 | 12/2014 | Damstra et al. |
| 8,951,293 | B2 | 2/2015 | Glazer et al. |
| 8,998,925 | B2 | 4/2015 | Schwappach |
| 9,216,045 | B2 | 12/2015 | Martineau et al. |
| 10,595,916 | B2 | 3/2020 | Hopkins et al. |
| 11,464,555 | B2 | 10/2022 | Hopkins |
| 2007/0142921 | A1 | 6/2007 | Lewis et al. |
| 2007/0233071 | A1 | 10/2007 | Dewey et al. |
| 2009/0317762 | A1 | 12/2009 | Schiefer et al. |
| 2010/0003638 | A1 | 1/2010 | Collins et al. |
| 2010/0003640 | A1 | 1/2010 | Damstra et al. |
| 2011/0060373 | A1 | 3/2011 | Russell et al. |
| 2011/0093020 | A1 | 4/2011 | Wu |
| 2011/0123951 | A1 | 5/2011 | Lomicka |
| 2012/0156646 | A1 | 6/2012 | Pelote |
| 2012/0246916 | A1* | 10/2012 | Farre Berga ......... A61C 8/0068 29/700 |
| 2013/0166033 | A1 | 6/2013 | Gunther |
| 2013/0226251 | A1* | 8/2013 | Chegini ............. A61B 17/8625 606/325 |
| 2014/0030675 | A1 | 1/2014 | Sanchez et al. |
| 2014/0031791 | A1 | 1/2014 | Russell et al. |
| 2014/0277183 | A1 | 9/2014 | Stalcup et al. |
| 2014/0336778 | A1 | 11/2014 | Termanini |
| 2015/0150687 | A1 | 6/2015 | Hopkins |
| 2015/0272646 | A1 | 10/2015 | Russell |
| 2016/0270922 | A1 | 9/2016 | Pressacco et al. |
| 2016/0367375 | A1 | 12/2016 | Boulris |
| 2018/0193074 | A1 | 7/2018 | Hopkins |
| 2020/0155212 | A1 | 5/2020 | Hopkins |

FOREIGN PATENT DOCUMENTS

| | | |
|---|---|---|
| CN | 110198679 A | 9/2019 |
| EP | 0099167 A1 | 1/1984 |
| JP | 2016513535 A | 5/2016 |
| JP | 2016538929 A | 12/2016 |
| WO | WO-9103213 A1 | 3/1991 |
| WO | WO-2018129247 A1 | 7/2018 |

OTHER PUBLICATIONS

"U.S. Appl. No. 15/862,931, Non-Final Action with Restriction Requirement mailed Sep. 3, 2019", 8 pgs.
"U.S. Appl. No. 15/862,931, Notice of Allowance mailed Nov. 7, 2019", 5 pgs.
"U.S. Appl. No. 15/862,931, Response filed Oct. 21, 2019 to Non-Final Office Action mailed Sep. 3, 2019", 10 pgs.
"U.S. Appl. No. 16/773,752, Final Office Action mailed Feb. 22, 2022", 11 pgs.
"U.S. Appl. No. 16/773,752, Non Final Office Action mailed Oct. 4, 2021", 11 pgs.
"U.S. Appl. No. 16/773,752, Notice of Allowance mailed Jun. 7, 2022", 5 pgs.
"U.S. Appl. No. 16/773,752, Preliminary Amendment filed Feb. 21, 2020", 5 pgs.
"U.S. Appl. No. 16/773,752, Response filed Jan. 4, 2022 to Non Final Office Action mailed Oct. 4, 2021", 12 pgs.
"U.S. Appl. No. 16/773,752, Response filed May 23, 2022 to Final Office Action mailed Feb. 22, 2022", 13 pgs.
"Australian Application Serial No. 2018205483, First Examination Report mailed Oct. 18, 2019", 3 pgs.
"Australian Application Serial No. 2018205483, Response filed Dec. 17, 2019 to First Examination Report mailed Oct. 18, 2019", 19 pgs.
"Canadian Application Serial No. 3,049,581, Office Action mailed Sep. 23, 2020", 4 pgs.
"Canadian Application Serial No. 3,049,581, Response filed Jan. 22, 2021 to Office Action mailed Sep. 23, 2020", 16 pgs.
"Chinese Application Serial No. 201880005677.0, Office Action mailed Jul. 28, 2021", w/ English Translation, 14 pgs.
"Chinese Application Serial No. 201880005677.0, Response filed Oct. 29, 2021 to Office Action mailed Jul. 28, 2021", w/ English claims, 8 pgs.
"European Application Serial No. 18701960.9, Response to Communication pursuant to Rules 161(1) and 162 EPC filed Mar. 2, 2020", 12 pgs.
"International Application Serial No. PCT/US2018/012478, International Preliminary Report on Patentability mailed Jul. 18, 2019", 9 pgs.
"International Application Serial No. PCT/US2018/012478, International Search Report mailed May 4, 2018", 5 pgs.
"International Application Serial No. PCT/US2018/012478, Written Opinion mailed May 4, 2018", 7 pgs.
"Japanese Application Serial No. 2019-537157, Examiners Decision of Final Refusal mailed Sep. 28, 2021", w/ English Translation, 5 pgs.
"Japanese Application Serial No. 2019-537157, Notification of Reasons for Refusal mailed Mar. 2, 2021", (W/ English Translation), 8 pgs.
"Japanese Application Serial No. 2019-537157, Response filed Jan. 27, 2022 to Examiners Decision of Final Refusal mailed Sep. 28, 2021", w/English claims, 13 pgs.
"Japanese Application Serial No. 2019-537159, Response filed Jun. 9, 2021 to Notification of Reasons for Refusal mailed Mar. 2, 2021", w/ English claims, 8 pgs.
"European Application Serial No. 18701960.9, Communication Pursuant to Article 94(3) EPC mailed Dec. 22, 2022", 7 pgs.
"European Application Serial No. 18701960.9, Response filed May 2, 2023 to Communication Pursuant to Article 94(3) EPC mailed Dec. 22, 2022", 12 pgs.

\* cited by examiner

POLY-AXIAL FIXATION POSTS

CLAIM OF PRIORITY

This patent application is a continuation of U.S. patent application Ser. No. 16/773,752, filed on Jan. 27, 2020, which is a divisional of U.S. patent application Ser. No. 15/862,931, filed on Jan. 5, 2018, now issued as U.S. Pat. No. 10,595,916, which claims the benefit of priority, under 35 U.S.C. Section 119(e), to ANDREW HOPKINS, U.S. Patent Application Ser. No. 62/444,148, entitled "POLY-AXIAL FIXATION POSTS," filed on Jan. 9, 2017, each of which is hereby incorporated by reference herein in its entirety.

TECHNICAL FIELD

The present disclosure relates generally to medical technology and in certain aspects to methods and systems for adjustably connecting a first orthopedic component to a second orthopedic component, e.g., a post to a glenoid baseplate.

BACKGROUND

Many orthopedic devices use screws to attach an implant (e.g., a plate) to bone. Implanted screws can relax, or otherwise release an initial compression between the implant and the bone, such that the screws can be limited to conferring a structural support role rather than maintaining implant compression.

OVERVIEW

The present disclosure provides, in certain examples described below, unique methods and systems for integrating or connecting orthopedic components. Each of these non-limiting examples can stand on its own or can be combined in various permutations or combinations with any one or more of the other examples.

Example 1 can include or use subject matter, such as a method, including a method of attaching an orthopedic device to a bone. The subject matter can comprise a method comprising, locating a baseplate on a glenoid of a patient, the baseplate including at least a first fastener bore extending through the baseplate, creating, by passing through the first fastener bore, a first post hole in the glenoid for locating a first fixation post within the glenoid, wherein the first fixation post includes a quasi-spherical head with a shaft extending therefrom to a distal end of the first fixation post, the quasi-spherical head including a textured outer surface for contacting at least a first wall of the first fastener bore, the first fixation post also including a porous metal sleeve received on the shaft, and driving the distal end of the first fixation post through the first fastener bore and into the first post hole such that an outer surface of the porous metal sleeve engages a surface of the first post hole and such that the textured outer surface of the quasi-spherical head contacts at least the first wall of the first fastener bore so as to removeably lock the quasi-spherical head to the baseplate, wherein said driving creates an initial compression between the baseplate and the glenoid, and wherein the porous metal sleeve is configured to receive bone ingrowth into the porous metal sleeve for maintaining said initial compression between the baseplate and the glenoid.

Example 2 can include, or can optionally be combined with the subject matter of Example 1 to optionally include, creating a first post hole in the glenoid by drilling.

Example 3 can include, or can optionally be combined with the subject matter of Example 1 or 2 to optionally include, drilling a first post hole using a drill bit in combination with a tool applying rotary motion to the drill bit to remove bone material from the first post hole.

Example 4 can include, or can optionally be combined with the subject matter of Examples 1-3 to optionally include, drilling a first post hole using a chisel tool in combination with a tool applying linear motion to the chisel tool to remove bone material from the first post hole.

Example 5 can include, or can optionally be combined with the subject matter of Examples 1-4 to optionally include, contacting at least the first wall of the first fastener bore with the textured outer surface of the quasi-spherical head by positioning at least a portion of a face of the textured outer surface of the quasi-spherical head against at least the first wall of the first fastener bore.

Example 6 can include, or can optionally be combined with the subject matter of Examples 1-5 to optionally include, driving the distal end of the first fixation post by applying an impact loading force to the quasi-spherical head of the first fixation post.

Example 7 can include, or can optionally be combined with the subject matter of Examples 1-6 to optionally include, driving the distal end of the first fixation post by applying a press loading force to the quasi-spherical head of the first fixation post.

Example 8 can include, or can optionally be combined with the subject matter of Examples 1-7 to optionally include, creating, by passing through a second fastener bore, a second post hole in the glenoid for locating a second fixation post within the glenoid, wherein the second fixation post includes a quasi-spherical head with a shaft extending therefrom to a distal end of the second fixation post, the quasi-spherical head including a textured outer surface for contacting at least a first wall of the second fastener bore, the second fixation post also including a porous metal sleeve received on the shaft, and driving the distal end of the second fixation post through the second fastener bore and into the second post hole such that an outer surface of the porous metal sleeve engages a surface of the second post hole and such that the textured outer surface of the quasi-spherical head engages at least the first wall of the second fastener bore so as to removeably lock the quasi-spherical head to the baseplate, wherein said driving creates an initial compression between the baseplate and the glenoid, wherein the porous metal sleeve is configured to receive bone ingrowth into the porous metal sleeve for maintaining said initial compression between the baseplate and the glenoid.

Example 9 can include, or can optionally be combined with the subject matter of Examples 1-8 to optionally include, a second fixation post that is aligned independently from the first fixation post.

Example 10 can include, or can optionally be combined with the subject matter of Examples 1-9 to optionally include, engaging at least the first wall of the second fastener bore with the textured outer surface of the quasi-spherical head by positioning at least a portion of a face of the textured outer surface of the quasi-spherical head against at least the first wall of the second fastener bore.

Example 11 can include, or can optionally be combined with the subject matter of Examples 1-10 to optionally include, driving the distal end of the second fixation post by applying an impact loading force to the quasi-spherical head of the second fixation post.

Example 12 can include, or can optionally be combined with the subject matter of Examples 1-11 to optionally include, driving the distal end of the second fixation post by applying a press loading force to the quasi-spherical head of the second fixation post.

Example 13 can include or use subject matter, such as a device. The subject matter can comprise a fixation post for attaching an orthopedic device to a bone comprising a quasi-spherical head with a textured outer surface, a shaft including a proximal end attached to the quasi-spherical head, a distal end opposite the proximal end, and a bearing surface between the proximal and distal ends, a porous metal sleeve including a central bore with a bore surface, the porous metal sleeve surrounding at least a portion of the shaft, wherein the bore surface substantially conforms with the beating surface, and a cap attached to the distal end of the shaft to retain the porous metal sleeve on the shaft.

Example 14 can include, or can optionally be combined with the subject matter of Example 13, to optionally include, the quasi-spherical head and the shaft forming a unitary core.

Example 15 can include, or can optionally be combined with the subject matter of Example 13 or 14 to optionally include, the porous metal sleeve having a proximal sleeve surface in contact with the quasi-spherical head and a distal sleeve surface in contact with the cap.

Example 16 can include, or can optionally be combined with the subject matter of Examples 13-15 to optionally include, an anti-rotation feature on the shaft.

Example 17 can include, or can optionally be combined with the subject matter of Examples 13-16 to optionally include, a generally elliptical cross-section of the shaft serving as an anti-rotation feature.

Example 18 can include, or can optionally be combined with the subject matter of Examples 13-17 to optionally include, the anti-rotation feature having a textured proximal cap surface configured to conform to the distal sleeve surface.

Example 19 can include, or can optionally be combined with the subject matter of Examples 13-18 to optionally include, a distal cap surface of the cap that is generally hemispherically shaped.

Example 20 can include, or can optionally be combined with the subject matter of Examples 13-19 to optionally include, a distal cap surface of the cap that is generally conically shaped.

This overview is intended to provide a summary of the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
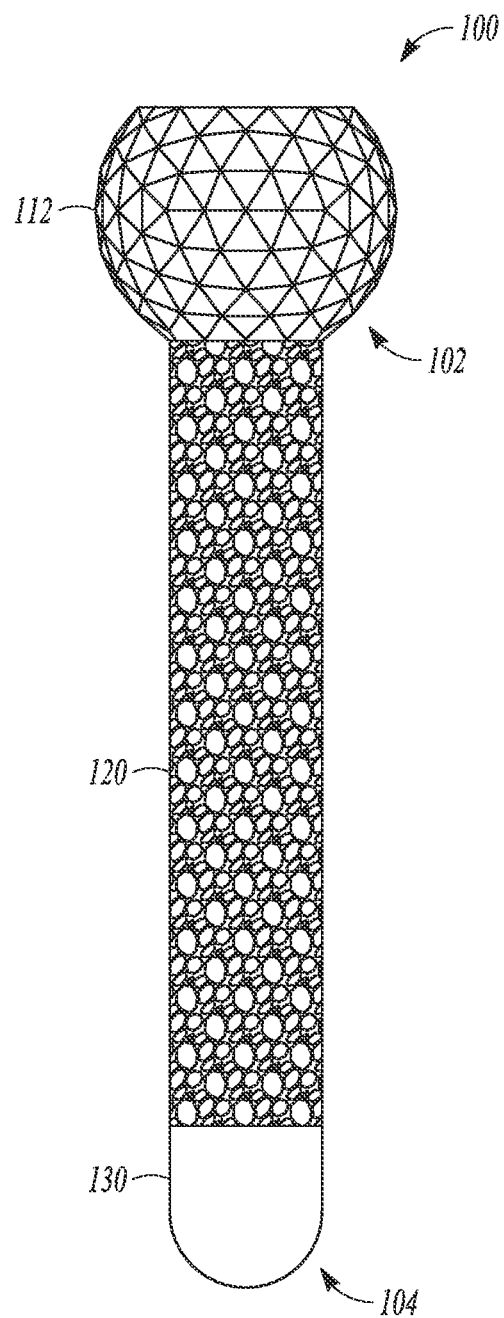
FIG. 1 shows a side view of an example fixation post.

FIG. 1 shows a side view of an exemplary fixation post 100. The fixation post 100 can be used to attach a surgical implant, such as a glenoid baseplate, to a patient, such as a bone of a patient. The fixation post 100 can include a core 110, a sleeve 120, such as a sleeve 120 that can be located around at least a portion of the core 110, and a cap 130 attached to the core 110, to retain the sleeve 120 on the core 110. The fixation post 100 can include a proximal end 102 and a distal end 104.

The core 110 can include a suitable fastener, such as at least one of a suitable surgical post, screw, and rod. The suitable fastener can include a head portion and a shaft portion attached to the head portion. A diameter of the head portion, such as a diameter measured perpendicular to a central axis extending along the longest dimension of the core 110, can be greater than the diameter of the shaft portion. In an example, a sleeve 120 can be located around the shaft portion of the core 110, such as an end of the sleeve 120 can contact the head portion of the core 110. A diameter of the cap 130, such as a diameter measured perpendicular to a central axis extending along the longest dimension of the core 110, can be greater than the diameter of the shaft portion. The cap 130 can be attached to the core 110, such as to the end of the shaft portion opposite the head portion, and contact the sleeve 120, such as the head portion and the cap 130 can retain the sleeve 120 on the shaft portion of the core 110.

Figure 2:
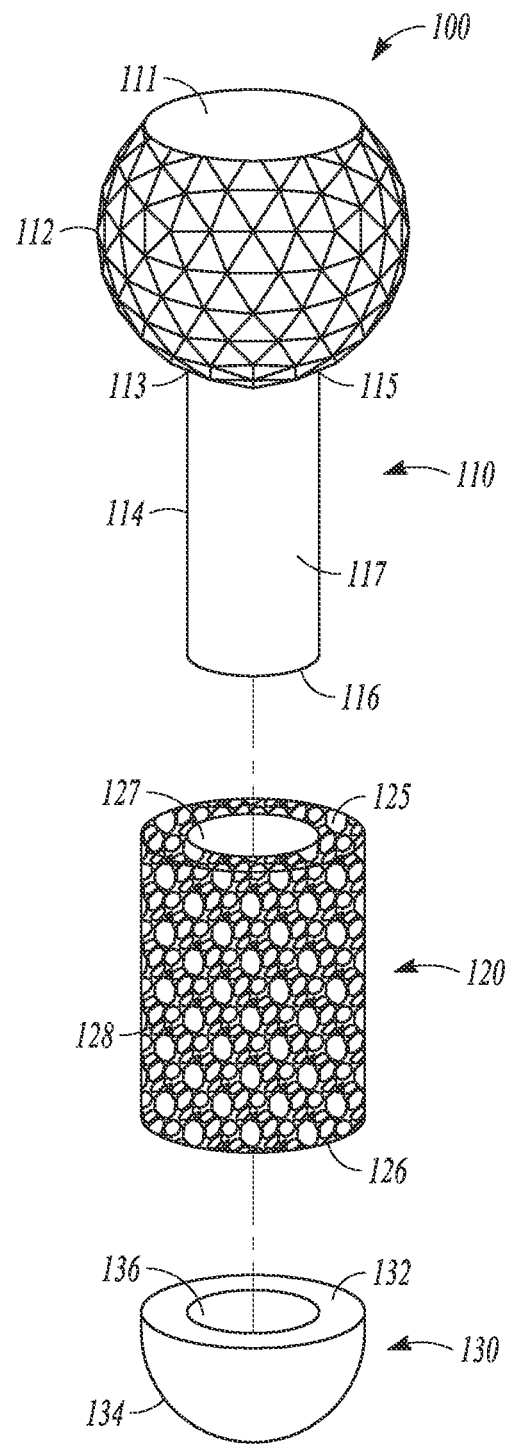
FIG. 2 shows an exploded isometric view of an example fixation post.

FIG. 2 shows an exploded isometric view of an exemplary fixation post 100. The core 110 can include a quasi-spherical head 112 and a shaft 114. The core 110 can include a unitary core, and the quasi-spherical head 112 and the shaft 114 can form an integrally formed single component.

The quasi-spherical head 112 can interact with a surgical implant, such as a wall of a fastener bore in a glenoid baseplate, to lock, such as removably lock, the quasi-spherical head 112 to the glenoid baseplate. The quasi-spherical head 112 can include a proximal head surface 111 and a distal head surface 113, such as a distal head surface 113 that can be generally parallel to the proximal head surface 111.

Figure 3A:
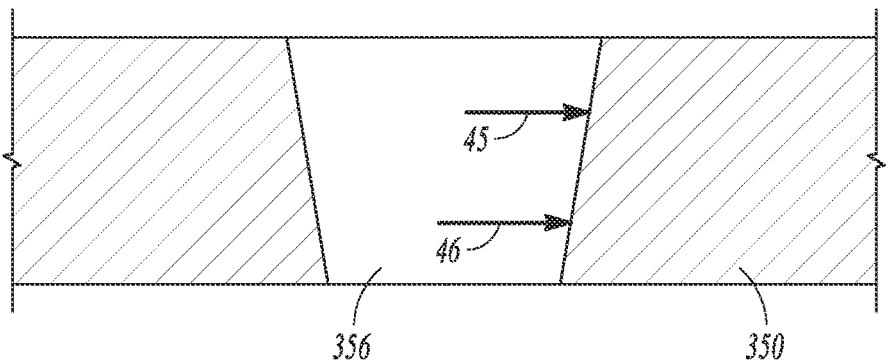
FIG. 3A shows a cross-section of an example plate.

FIG. 3A shows a cross-section of an exemplary plate 350, such as a glenoid baseplate. The plate 350 can include a fastener bore 356. A suitable bore can be tapered or non-tapered. In this instance, the fastener bore 356 can be tapered, to include a first radius 45 positioned near the top or entrance into the fastener bore 356 and a second radius 46 positioned near the bottom or exit from the fastener bore 356. Optionally, the first radius 45 and the second radius 46 can be related to measurements on the quasi-spherical member 20 (See FIG. 3C). A suitable bore can be or incorporate any suitable three-dimensional shape, e.g., incorporating rectilinear and/or curvilinear features. A suitable bore can have a frustoconical shape. Suitable shapes of a female-type bore can be or include full and partial forms of wedges, tapered bodies, toroids, conoids, catenoids, cubes, parallelepipeds, prisms, and combinations of the same. Suitable shapes can include, but are not limited to, full or partial cylinders, cuboids, cones, pyramids, and tetrahedrons, and combinations of the same. A quasi-spherical member 20 with a textured outer surface, such as quasi-spherical head 112, and a bore, such as a fastener bore 356 into which the quasi-spherical member 20 can be received, can be any of those disclosed in commonly-owned U.S. application Ser. No. 14/557,763, which was filed on Dec. 2, 2014, and which is titled "Adjustable Orthopedic Connections" and which is hereby incorporated by reference in its entirety.

Figure 3B:
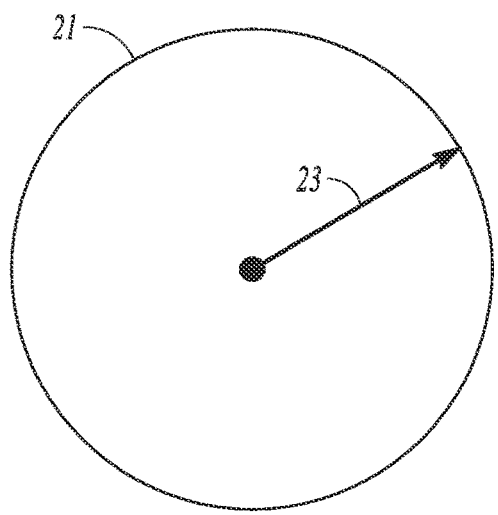
FIG. 3B shows a radius of a perfect sphere.
Figure 3C:
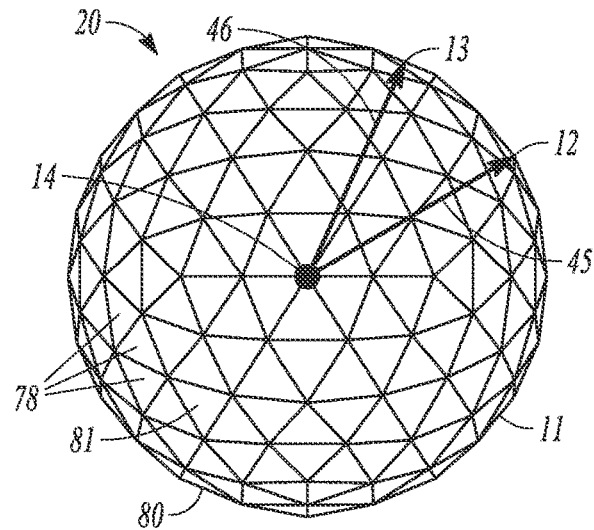
FIG. 3C shows a quasi-spherical member with a textured outer surface according to one embodiment of the present disclosure.

FIG. 3B shows a perfect sphere 21 having a radius 23. FIG. 3C illustrates a quasi-spherical member 20, such as at least a portion of a quasi-spherical head 112 that includes an illustrative textured outer surface 11 covering essentially the entirety of the quasi-spherical member 20. In accordance with certain aspects of the present disclosure, quasi-spherical members or other male-type connectors in accordance with the present disclosure can incorporate a textured outer surface covering more than 50%, or more than 65%, or more than 75%, or more than 85% of the quasi-spherical member 20 or another connector. In some instances, the textured outer surface 11 can cover between about 25% and about 50% of the quasi-spherical member 20 or another connector, or between about 35% and about 75%, or between about 50% and about 90%, or between about 60% and about 100%.

Continuing with FIG. 3C, this particular textured outer surface 11 can incorporate a three-dimensional tessellation 80. A suitable tessellation can incorporate a plurality of polygonal elements, such as polygonal elements 78. In this particular instance, the polygonal elements are triangular elements or faces 81. Textured outer surfaces according to additional aspects of the present disclosure can incorporate other suitable three-dimensional tessellations. In certain embodiments, quasi-spherical members or other male-type connectors in accordance with the present disclosure will mimic or approximate a plurality of stacked polyhedra such as but not limited to stacked cubes, rhombic dodecahedrons, truncated octahedrons, hexagonal prisms, or triangular prisms. In some forms, quasi-spherical members or other male-type connectors in accordance with the present disclosure can mimic or approximate a honeycomb of polyhedral cells including uniform and non-uniform honeycombs.

Continuing with FIG. 3C, the textured outer surface 11 can include a plurality of outermost extensions 12 which in this illustrative embodiment occur at vertices of the triangular faces as discussed hereinbelow. A distance from the center of the quasi-spherical member 20 to an outermost extension 12 can be equal to the first radius 45. While not necessary, an arc connecting at least two of the outermost extension 12 can have generally the same curvature as the arc of the perfect sphere 21. The textured outer surface 11 can include a plurality of innermost depressions 13 which in this illustrative embodiment occur at the centers of the triangular faces as discussed hereinbelow. A distance from the center of the quasi-spherical member 20 to an innermost depression 13 can be equal to the second radius 46. While not necessary, an arc connecting at least two of the innermost depressions can have generally the same curvature as the arc of the perfect sphere 21. A secure grip between the textured outer surface 11 and the wall of the fastener bore can occur at one or more interfaces 22. While not necessary, the relationship between the first radius 45 and the second radius 46 can be as follows: where R=a radius 23 of a perfect sphere 21, the first radius 45=R+t and the second radius 46=R−t, where "t" is a variable that can be changed to create variable textured surfaces 11.

Figure 4A:
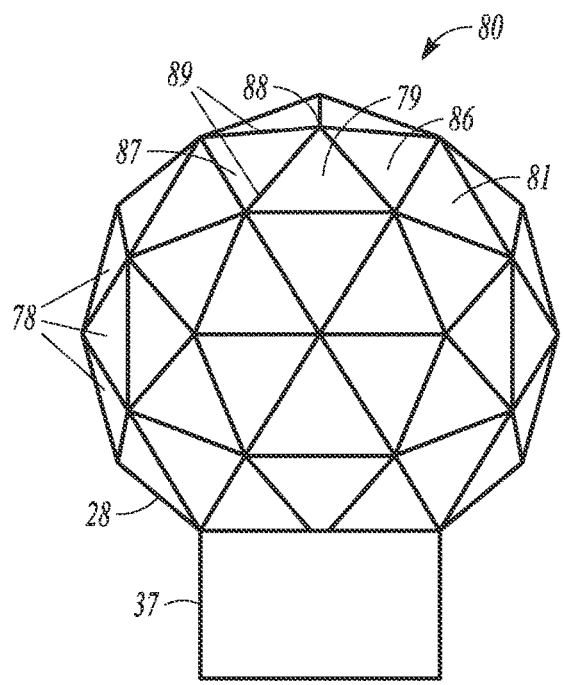
FIGS. 4A-4D show examples of quasi-spherical members with textured outer surfaces of different densities.
Figure 4B:
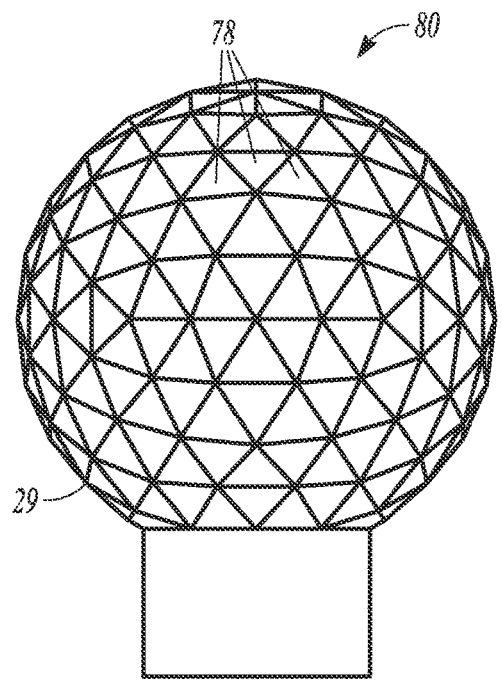
Figure 4C:
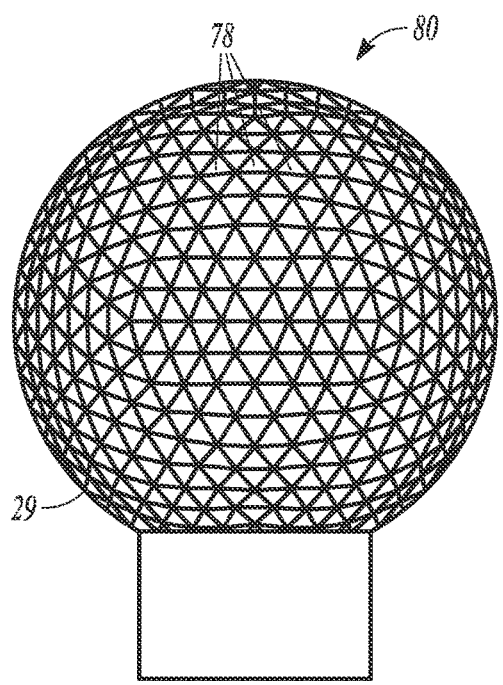
Figure 4D:
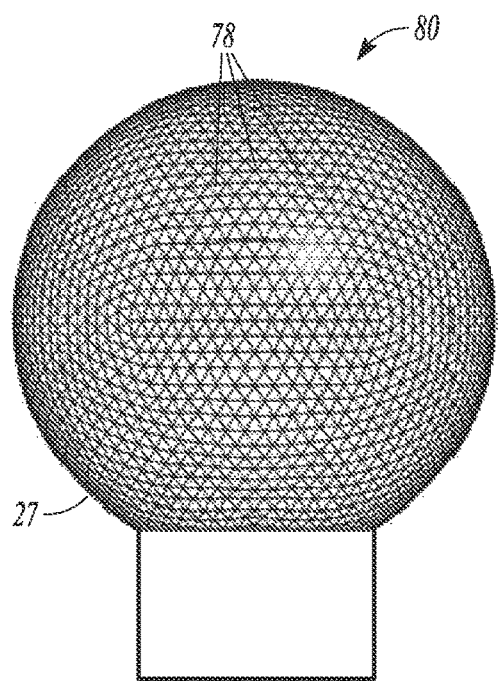

FIGS. 4A-D illustrate a spectrum of densities of tessellation patterns 80. FIG. 4A provides a quasi-spherical member 20 with a low density 28 of polygonal elements 78. FIG. 4D provides a quasi-spherical member 20 with a high density 27 of polygonal elements 78. FIGS. 4B-4C illustrate quasi-spherical members 20 with lower and higher intermediate densities 29 of polygonal elements 78. A quasi-spherical member 20 with a higher density can allow a higher quality of spherical mapping. As the quasi-spherical member 20 can be adjusted in the fastener bore, the higher quality mapping can allow a greater spectrum of possible orientations or angular positions of the quasi-spherical head 112 in relation to the baseplate.

FIG. 4A shows features of the polygonal surface elements 78. An individual polygon 86 can have an exterior face 87 that forms an outer surface on the quasi-spherical member 20. The exterior face 87 can include a chord 89 as an edge of the exterior face 87. Each cord 89 can be contiguous with a chord 89 of a neighboring polygon 79. The chord 89 can terminate at each end in a vertex 88. Each vertex 88 of a polygon 86 can be contiguous with a vertex 88 of a neighboring polygon 79. Any number of these exterior surface features (e.g., edges, chords, planar or non-planar faces, vertices, etc.) and/or any of the other exterior surface features disclosed herein that can be incorporated into a textured outer surface of a connecting member can forcibly contact walls or surfaces in a bore to some degree, and in some instances, can be formed with materials that cause such surface features to be crushed or to otherwise deform upon such forcible contact, to removeably lock or help to removeably lock the male-type connecting member in the bore. In an example, a plurality of planar or nearly planar faces on a textured outer surface of a connecting member (e.g., a quasi-spherical member) can each partially contact a curved wall of a bore e.g., cylindrical or conical).

In accordance with certain aspects of the present disclosure, quasi-spherical members or other male-type connectors in accordance with the present disclosure can incorporate a textured outer surface that can include a plurality of generally planar surfaces, for example, where the combined area of the generally planar surfaces cover more than 50%, or more than 65%, or more than 75%, or more than 85% of the quasi-spherical member or another male-type connecting member. In some instances, the combined area of the generally planar surfaces can cover between about 25% and about 50% of the quasi-spherical member or other male-type connecting member, or between about 35% and about 75%, or between about 50% and about 90%, or between about 60% and about 100%.

The quasi-spherical head 112 can include the quasi-spherical member 20, such as at least a portion of the volume of the quasi-spherical member 20. In an example, the quasi-spherical head 112 can include a portion of the volume of the quasi-spherical member 20, such as a volume in a range of approximately 25% to 100% of the volume of the quasi-spherical member 20, such as about 30%, 35%, 40%, 45%, 50%, 55%, 60%, 65%, 70%, 75%, 80%, 85%, 90%, 95%, and 100% of the volume of the quasi-spherical member 20.

Referring again to FIG. 2, the shaft 114 can provide mechanical support for the fixation post 100, such as when the fixation post 100 can act as a fastener. The shaft 114 can include a proximal shaft end 115, a distal shaft end 116 opposite the proximal shaft end 115, and a bearing surface 117, such as a surface of the shaft 114 extending between the proximal shaft end 115 and the distal shaft end 116. The shaft 114 can include a central axis extending along the longest dimension of the shaft 114, such as an axis extending through the centroid of a cross-sectional area of the shaft 114 perpendicular to the central axis, such as one or more cross-sectional areas. The cross-sectional area can include areas that are symmetric, such as a circle or an ellipse, or asymmetric. In an example, the shaft 114 can include a right circular cylinder, such as a shaft 114 with a circular cross-section, or a right ellipsoidal cylinder, such as a shaft 114 with an elliptical cross-section.

The shaft 114 can be constructed of a biocompatible material, such as one or more biocompatible materials. A bi° compatible material can include ceramics, synthetic polymeric materials, and metallic materials, such as titanium, a titanium alloy, cobalt chromium, cobalt chromium molybdenum, tantalum, a tantalum alloy, stainless steel, or a combination thereof.

The sleeve 120 can surround at least a portion of the core 110, such as at least a portion of the shaft 114. The sleeve 120 can provide a surface, such as an external surface, to attach to a patient interface surface, such as a wall of a hole in a patient bone. The hole in the patient bone can be configured to receive the fixation post 100 to secure the fixation post 100 to the patient bone, such as to provide an initial compression between two components connected by the fixation post 100, such as between a baseplate and the patient bone. The sleeve can provide a surface, such as a porous surface, for the ingrowth of tissue, such as bone tissue, to retain the fixation post 100 within the patient bone, to maintain the initial compression between the baseplate and the patient bone while the patient heals. The sleeve 120 can include a proximal end surface 125, a distal end surface 126 generally parallel to the proximal end surface 125, a central bore with a bore surface 127, such as a bore surface 127 that substantially conforms with the bearing surface 117 of the shaft 114, and an exterior surface 128, that can be in contact with the patient bone.

The sleeve 120 can substantially conform to the shaft 114, or in other words the bore surface 127 can substantially conform to the bearing surface 117 of the shaft 114, to distribute loads transmitted from the shaft 114 to the sleeve 120. "Substantially conform" can describe the amount of contact interface between two surfaces, such as the bearing surface 117 and the bore surface 127, to form an interface between the bore surface 127 and the bearing surface 117. The sleeve 120 can substantially conform to the shaft 114, such as when a substantial portion of the bore surface 127 can contact the bearing surface 117 of the shaft 114. A substantial portion of the bore surface 127 can include a range of approximately 50% to 100% of the bore surface 127, such as approximately 60%, 70%, 80%, 90%, or 100% of the bore surface 127. In an example, a shaft 114 with a, first set of physical dimensions, such as diameter, length, and taper of the shaft 114, and a bore surface 127, such as with generally the same first set of physical dimensions as the shaft 114, can substantially conform to one another, such as when locating the bore surface 127 on the bearing surface 117, such as by sliding the sleeve 120 onto the shaft 114. The distal shaft end. 116 can be approximately parallel with the distal end surface 126 of the sleeve 120 or protrude from the distal end surface 126, such as to receive the cap 130.

The sleeve 120 can be located on the core 110 to minimize motion between the sleeve 120 and the shaft 114. Minimizing motion can contribute to maintaining a compressive force between the surgical implant and the patient bone, to preserve ingrowth of bone tissue into the sleeve 120 and more permanently integrate the fixation post 100 into the patient bone.

Longitudinal motion can occur between the sleeve 120 and the shaft 114, such that the sleeve 120 can move with respect to the shaft 114 in a direction along the central axis of the shaft 114. Longitudinal motion can be minimized, such as by locating the sleeve 120 snugly between the quasi-spherical head 112 and the cap 130. In an example, the sleeve 120 can be located on the core 110 and substantially conform to the shaft 114. The cap 130 can be attached to the shaft 114, such as at the distal shaft end 116, and against the distal end surface 126 of the sleeve 120, such as to locate the proximal end surface 125 of the sleeve 120 against the distal head surface 113, so as to minimize linear motion of the sleeve 120 along the central axis of the shaft 114.

Rotational motion can occur between the sleeve 120 and the shaft 114, such that the sleeve 120 can rotate about the shaft 114. Rotational motion can be minimized, such as with the use of an anti-rotation feature, such as a characteristic of the fixation post 100 that can be configured to inhibit rotational motion. In an example, the shaft 114 can be configured with a non-circular cross-section, such as an elliptical cross-section, and the bore surface 127 of the sleeve 120 can substantially conform to the non-circular cross-section. Rotational forces applied to the sleeve 120 can be resisted by opposing forces created by the shaft 114, such as forces created near the major vertices of the elliptical cross-section at the interface between the sleeve 120 and the shaft 114, to minimize rotational motion of the sleeve 120 about the shaft 114.

Figure 5A:
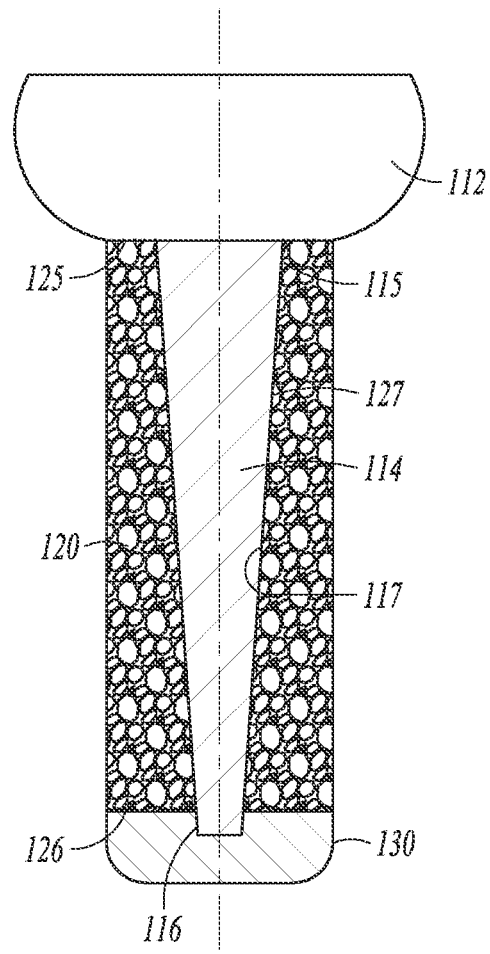
FIG. 5A shows a cross-section of a first exemplary fixation post.
Figure 5B:
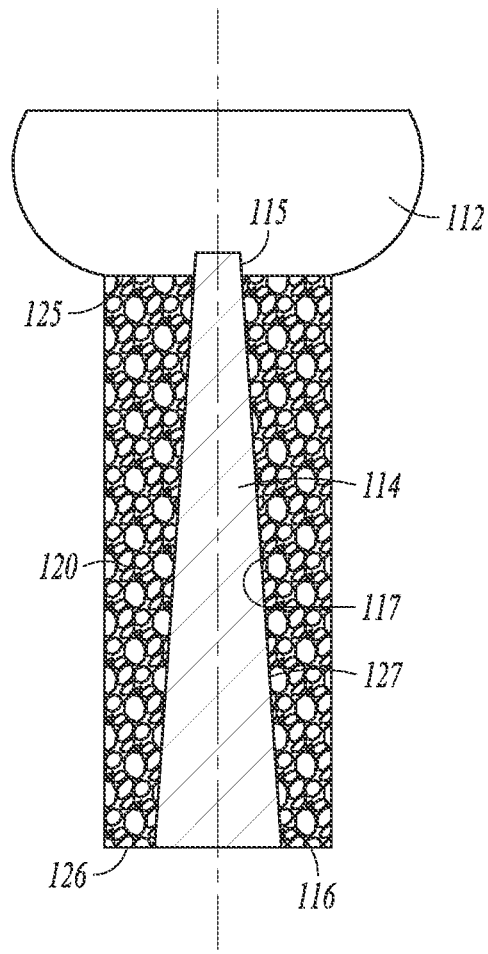
FIG. 5B shows a cross-section of a second exemplary fixation post.

FIGS. 5A & 5B show cross-sections of a first exemplary fixation post 100 and a second exemplary fixation post 100, respectively. The cross-sectional area defining the shaft 114, such as the cross-sectional area of the shaft 114 perpendicular to the central axis of the shaft 114, can vary in planar area along the central axis of the shaft 114, such that the cross-sectional area at any location along the central axis can have a planar area different from any other cross-sectional area along the central axis. The planar areas can vary uniformly along the central axis.

As shown in FIG. 5A, the proximal shaft end 115 can include a first planar area, the distal shaft end 116 can include a second planar area, such as the first planar area can be greater than the second planar area, and successive planar areas along the shaft 114 between the proximal shaft end 115 and the distal shaft end 116 can decrease, such as at a uniform rate. For example, the shaft 114 can include a positive tapered shaft, such as a frustoconical shaped shaft, with a circular cross-sectional area at the proximal shaft end 115 greater than a circular cross-sectional area at the distal shaft end 116. In an example, the bore surface 127 can contact the shaft 114 at the bearing surface 117, and a cap 130 can retain the sleeve 120 against the shaft 114.

The sleeve 120 can be located on a shaft 114, such as a positive tapered shaft, to decrease or minimize motion between the sleeve 120 and the shaft 114. In an example, the sleeve 120 can be located on the positive tapered shaft, such as by sliding the central bore of the sleeve 120 onto the shaft 114 by inserting the distal shaft end 116 into the central bore at the proximal end surface 125, and sliding the positive tapered shaft into the central bore until the distal shaft end 116 can be parallel with or protrude from the distal end surface 126. In doing so, the bore surface 127 can substantially conform to the positive taper of the shaft 114, to retain the sleeve 120 on the shaft 114. The cap 130 can be attached to the shaft 114, such as at the distal shaft end 116, and against the distal end surface 126 of the sleeve 120, such as to locate the bore surface 127 of the sleeve 120 against the bearing surface 117, so as to minimize at least one of longitudinal and rotational motion of the sleeve 120 with respect to the shaft 114.

As shown in FIG. 511, the proximal shaft end 115 can include a first planar area, the distal shaft end 116 can include a second planar area, and the first planar area can be less than the second planar area, and successive planar areas along the shaft 114 between the proximal shaft end 115 and the distal shaft end 116 can increase, such as at a uniform rate. For example, the shaft 114 can include a negatively tapered shaft, such as a frustoconical shaped shaft, with a circular cross-sectional area at the proximal shaft end 115 less than a circular cross-sectional area at the distal shaft end 116. In an example, the bore surface 127 can contact the shaft 114 at the bearing surface 117, such as the device 100 does not require a cap 130 to retain the sleeve 120 on the shaft 114.

The sleeve 120 can be located on a shaft 114, such as a negatively tapered shaft, to minimize motion between the sleeve 120 and the shaft 114. In an example, the sleeve 120 can be located on the negative tapered shaft, such as by sliding the central bore of the sleeve 120 onto the shaft 114 by inserting the proximal shaft end 115 into the central bore at the distal end surface 126, and sliding the negative tapered shaft into the central bore until the proximal shaft end 115 can be parallel with or protrude from the proximal end surface 125. In doing so, the bore surface 127 can substantially conform to the negative taper of the shaft 114, to retain the sleeve 120 on the shaft 114. The quasi-spherical head 112 can be attached to the shaft 114, such as at the proximal shaft end 115, and against the proximal end surface 125 of the sleeve 120, such as to locate the bore surface 127 of the sleeve 120 against the bearing surface 117, so as to minimize at least one of longitudinal and rotational motion of the sleeve 120 with respect to the shaft 114.

In an example, the bore surface 127 of the sleeve 120 can be covered with a material, such as a biocompatible material, configured to increase the surface area of the bore surface 127 available to substantially conform with the shaft 114, so as to further minimize at least one of longitudinal and rotational motion of the sleeve 120 with respect to the shaft 114. For example, a porous bore surface 127 of the sleeve 120 can be covered, or otherwise coated, with a biocompatible material, such as to fill in voids presented by the bore surface 127 to the bearing surface 117, so as to increase the contact interface area formed between the bore surface 127 and the bearing surface 117.

The sleeve 120 can be constructed of one or more biocompatible materials. The biocompatible material can include a porous material, such as a porous metal material configured to promote ingrowth of bone or soft tissue therein, to improve osseointegration onto at least a portion of the fixation post 100, such as the sleeve 120. The porous material can increase short-term stability of the implant within the bone by an increase in frictional engagement of the porous material with the surrounding bone after implanting the fixation post 110 into a post hole in the patient bone. The porous material can approximate the microstructure of a natural cancellous bone thereby providing an osteoconductive matrix for the incorporation of bone growth, such as by providing optimal permeability and high surface area to encourage new bone ingrowth into the pores of the porous scaffold of the porous material. The porous material can include metallic materials, such as titanium beads, and materials applied with a plasma spray. The porous material can include a Trabecular Metal™ material, a porous tantalum material marketed by Zimmer, Inc., as disclosed in several U.S. patents, including, U.S. Pat. Nos. 5,282,861, 5,443,515, and 6,063,442, the disclosures of which are incorporated herein by reference.

The cap 130 can retain the sleeve 120 to the core 110. The cap 130 can include a proximal cap surface 132 and a distal cap surface 134. The cap 130 can interface to the core 110 at the distal shaft end 116 of the shaft 114. The distal shaft end 116 can attach to the cap 130 at the proximal cap surface 132. The distal shaft end 116 can be attached to the proximal cap surface 132 by at least one of an adhesive connection, such as with the use of an epoxy, a welded connection, such as a friction weld, and a friction connection, such as an interference fit, by press fitting the cap 130 to the distal shaft end 116.

The cap 130 can include a cap hole 136 in the proximal cap surface 132. The cap hole 136 can include any depression in the proximal cap surface 132, such as at least one of a slot and a circular hole. The distal shaft end 116 can attach to the cap 130 by an interface between the distal shaft end 116 and the cap hole 136. The distal shaft end 116 can interface to the cap 130 by at least one of a threaded connection, a friction connection between the distal shaft end 116 and the cap hole 136, an adhesive connection, and a welded connection.

The proximal cap surface 132 can include a surface configured to interface with the sleeve 120, such as the distal end surface 126 of the sleeve 120. The proximal cap surface 132 can conform to the distal end surface 126 by being generally parallel to, or in a unitary plane with, the distal end surface 126. The proximal cap surface 132 can include a textured surface, such as a textured outer surface including a tessellated surface incorporating a three-dimensional tessellation 80. In an example, the proximal cap surface 132 can conform to the distal end surface 126, or the textured surface can interface with the distal end surface 126, to form a friction interface to minimize rotational motion of the sleeve 120 about the shaft 114.

The distal cap surface 134 can include a surface configured to interface with the patient bone at a fastener bore created in the patient bone. The distal cap surface 134 can be configured to assist insertion of the fixation post 100 into the patient bone by having the distal cap surface 134 include a generally convex shape. The generally convex shape can include at least one of a generally rounded shape, such as the generally rounded shape shown in FIG. 2, a generally conical shape with tapered surfaces or right circular cylindrical surfaces, and a combination of generally, rounded and generally conical shapes, such as a generally convex shape including rounded and conical portions.

The cap 130 can be made of a biocompatible material. The cap 130 can be formed from a biocompatible material that can retain a generally smooth shape, such as the distal cap surface 134 can be generally smooth, such as to ease insertion of the fixation post 100 into the patient bone. For example, the distal cap 130 can be made of ceramic, synthetic polymeric materials, or metallic materials, such as titanium, a titanium alloy, cobalt chromium, cobalt chromium molybdenum, tantalum, a tantalum alloy, stainless steel, or a combination thereof.

Figure 6:
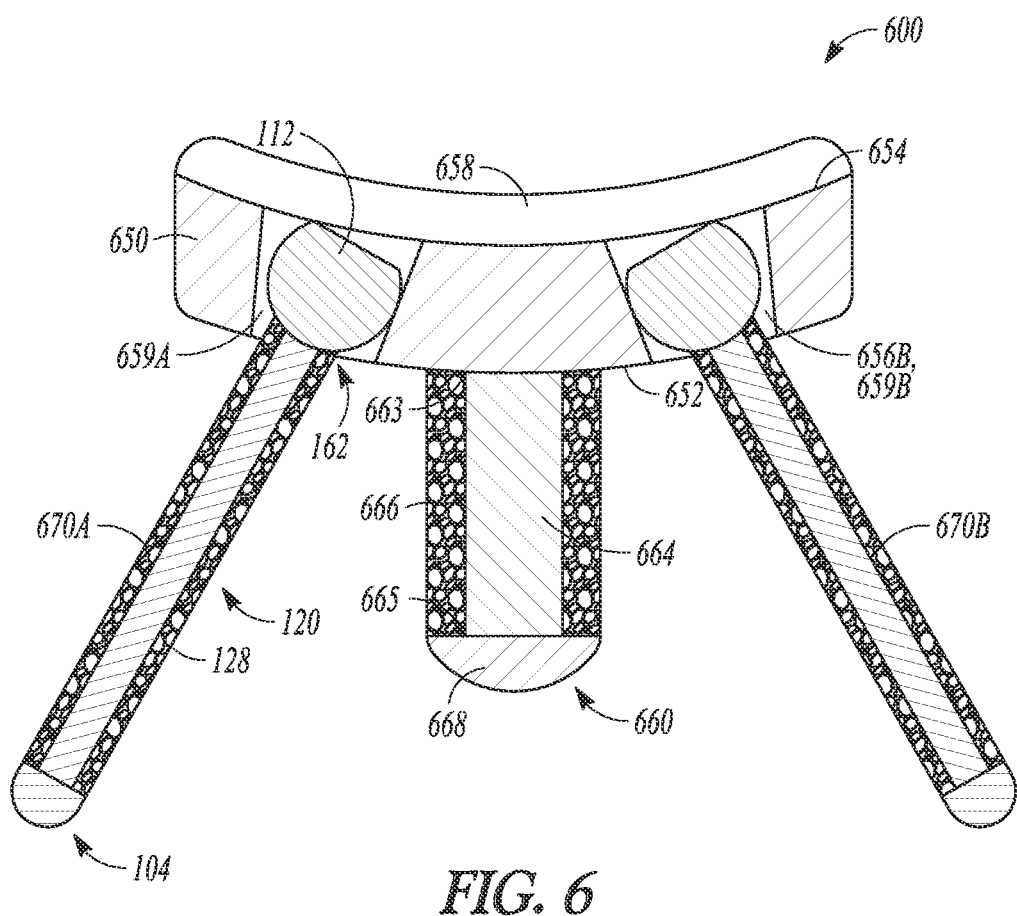
FIG. 6 shows a cross-section of an example orthopedic implant assembly 600.

FIG. 6 shows a cross-section of an exemplary orthopedic implant assembly 600. The orthopedic implant assembly 600 can include a baseplate 650, a spacer 658, and a fixation post 670, such as a first fixation post 670A and a second fixation post 670B.

The baseplate 650 can include a patient-contacting surface 652, or a surface of the baseplate 650 that can be located against the patient bone, or facing the bone; a spacer surface 654, or a surface of the baseplate 650 generally parallel or opposite to the patient-contacting surface 652 and facing away from the patient bone; a central post 660 that can be attached to the patient-contacting surface 652; and a fastener bore 656, such as a first fastener bore 656A and a second fastener bore 656B. The fastener bore 656 can extend through the base plate 650, such as from the spacer surface 654 to the patient-contacting surface 652. The fastener bore 656 can include a wall 659 or a surface connecting the spacer surface 654 to the patient-contacting surface 652. The fastener bore 656 can include at least one wall 659, or more specifically the first fastener bore 656A can include a first wall 659A and the second fastener bore 656B can include a second wall 659B. The spacer 658 can be attached, such as removably attached; to the spacer surface 654.

The central post 660 can anchor the base plate 650 to the patient bone, such as the glenoid. The central post 660 can be similar to the fixation post 100, in that it can possess similar components and be of similar construction as the fixation post 100. The central post 660 can include a central shaft 664 with a proximal central shaft end 663, a distal central shaft end 665, a central sleeve 666, such as a porous metal sleeve, surrounding at least a portion of the central shaft 664, and a central cap 668 attached to the distal central shaft end 665. The proximal central shaft end 663 can attach to the baseplate 650. In an example, the central post 660 can include a central quasi-spherical head (not shown), and the proximal central shaft end 663 can attach to the central quasi-spherical head. In an example, the central post 660 with the central quasi-spherical head can be located in a central fastener bore (not shown), such as a central fastener bore similar to the fastener bore 656 and located in the baseplate 650. In an example, a portion of the central quasi-spherical head can contact the central fastener bore, and the central sleeve 666 can engage the glenoid by engaging a surface of a central post hole, such as a central post hole created in the glenoid and configured to accommodate the central post 660.

The fixation post 670 can secure the baseplate 650 to the patient bone, such as the glenoid, by creating an initial compression between the baseplate 650 and the glenoid and maintaining the initial compression during patient recovery from implant surgery, for example. The proximal end 102 of the fixation post 670 can be located in the fastener bore 656, and the quasi-spherical head 112 can contact the fastener bore 656. The sleeve 120 of the fixation post 670 can engage the glenoid, or a surface of a post hole created in the glenoid and configured to accommodate the distal end 104 of the fixation post 670, or by engaging bone cement inserted into the post hole. The post hole can include at least one of a first post hole to accept the first fixation post 670A, and a second post hole to accept the second fixation post 670B.

The quasi-spherical head 112 can interact with the fastener bore 656 to removably lock the quasi-spherical head 112 to the baseplate 650. In some instances, forcible contact between the quasi-spherical head 112 and walls of the bore will be sufficient to crush or otherwise deform surface features of the quasi-spherical head and/or surfaces or walls within the bore. The shape of the bore 656 including its walls and the shape and surface features of the quasi-spherical head 112 can be such that the quasi-spherical head can be positionable in the bore for removably locking the quasi-spherical head 112 to the base plate 650, thereby providing a fixed, immovable connection between the quasi-spherical head 112 and the baseplate 650.

In an example, the quasi-spherical head 112 of the first fixation post 670A can contact the first wall 659A of the first fastener bore 656A and the external surface 128 of the sleeve 120 can contact a surface of the first post hole, so as to create an initial compression between the baseplate 650 and the patient bone and to allow for the ingrowth of bone tissue into the sleeve 120 to maintain the initial compression. In an example, the quasi-spherical head 112 of the second fixation post 670B can contact the second wall 659B of the second fastener bore 656B and the external surface 128 of the sleeve 120 can contact a surface of the second post hole.

The quasi-spherical head 112 can be configured to interact with the fastener bore 656, and contact between the quasi-spherical head 112 and the fastener bore 656 can cause at least one of the quasi-spherical head 112, and the fastener bore 656 to deform. The quasi-spherical head 112 can be constructed of a material with a first hardness, and the base plate 650 can be constructed of a material with a second hardness. In an example, the first hardness can be greater than the second hardness, such that contact between the quasi-spherical head 112 with the wall 659 can cause the wall 659 to deform, thereby removably locking the quasi-spherical head 112 to the baseplate 650. In an example, the second hardness can be greater than the first hardness, such that contact between the quasi-spherical head 112 and the wall 659 can cause the quasi-spherical head 112 to deform, thereby removably locking the quasi-spherical head 112 to the baseplate 650.

Based on the orientation shown in FIG. 6, placement of the fixation posts generally occurs in a downward direction, i.e., the leading ends of the posts enter the fastener bores through the larger top ends of the bores and exit the smaller bottom ends. Thereafter, the posts can be advanced (e.g., into bone) until the quasi-spherical heads are received down into the respective female bores and locked therein. Alternatively, each fastener bore 656 can be modified so the larger end, such as with a first radius 45, is positioned at the patient-contacting surface 652 and the smaller end, such as with a second radius 46, is positioned at the spacer surface 654. Such a design can facilitate an implantation method in which the baseplate 650 is driven down onto the fixation posts 670 after the fixation posts 670 are driven into the bone so that the quasi-spherical heads 112 enter the fastener bores 656 through the larger bottom ends of the bores 656 and move a distance in the fastener bores 656 toward the smaller top ends until the baseplate 650 can be suitably locked in place. Alternatively, such a design can facilitate an implantation method in which the fixation posts 670 are positioned in the base plate 650 and then the baseplate 650 and fixation posts 670 are then driven onto the bone until distal ends of the fixation posts are suitably locked in place in the bone and proximal ends 104 of the fixation posts 670 are suitably locked in the fastener bores 656.

The fixation post 100 can be assembled with an exemplary first post assembly method. A quasi-spherical head 112 and a shaft 114 can be received. The shaft 114 can be attached to the quasi-spherical head 112 to form a core 110. In an example, the quasi-spherical head 112 and the shaft 114 can be received as a single component, such as a unitary core. The core 110 can receive the sleeve 120 by inserting the core 110 into the central bore of the sleeve 120, and the bore surface 127 can substantially conform to the bearing surface 117 of the shaft 114. The distal shaft end 116 can be approximately flush with the distal end surface 126, or be proximal to, or protrude from the distal end surface 126. A cap 130 can be attached to the distal shaft end 116 to retain the sleeve 120 on the shaft 114, such as between the quasi-spherical head 112 and the cap 130.

The fixation post 100 can be assembled with an exemplary second post assembly method. A shaft 114, such as a negative taper shaft, can be received. The negative taper shaft can receive the sleeve 120 by inserting the negative taper shaft into the central bore of the sleeve 120 and the bore surface 127 of the sleeve 120 can substantially conform to the bearing surface 117 of the shaft 114. In an example, the proximal shaft end 115 can be inserted into the central bore of the sleeve 120 at the distal end surface 126 and advanced into the central bore until the proximal shaft end 115 is flush with, is proximal to, or protrudes from the proximal end surface 125. The bore surface 127 can substantially conform to the bearing surface 117 or the negative taper of the shaft 114, to prevent the sleeve 120 from moving further distally along the central axis of the shaft 114. A quasi-spherical head 112 can be attached to the proximal shaft end 115, to retain the sleeve 120 on the shaft 114, such as between the quasi-spherical head 112 and the bearing surface 117 of the negative taper shaft.

Figure 7:
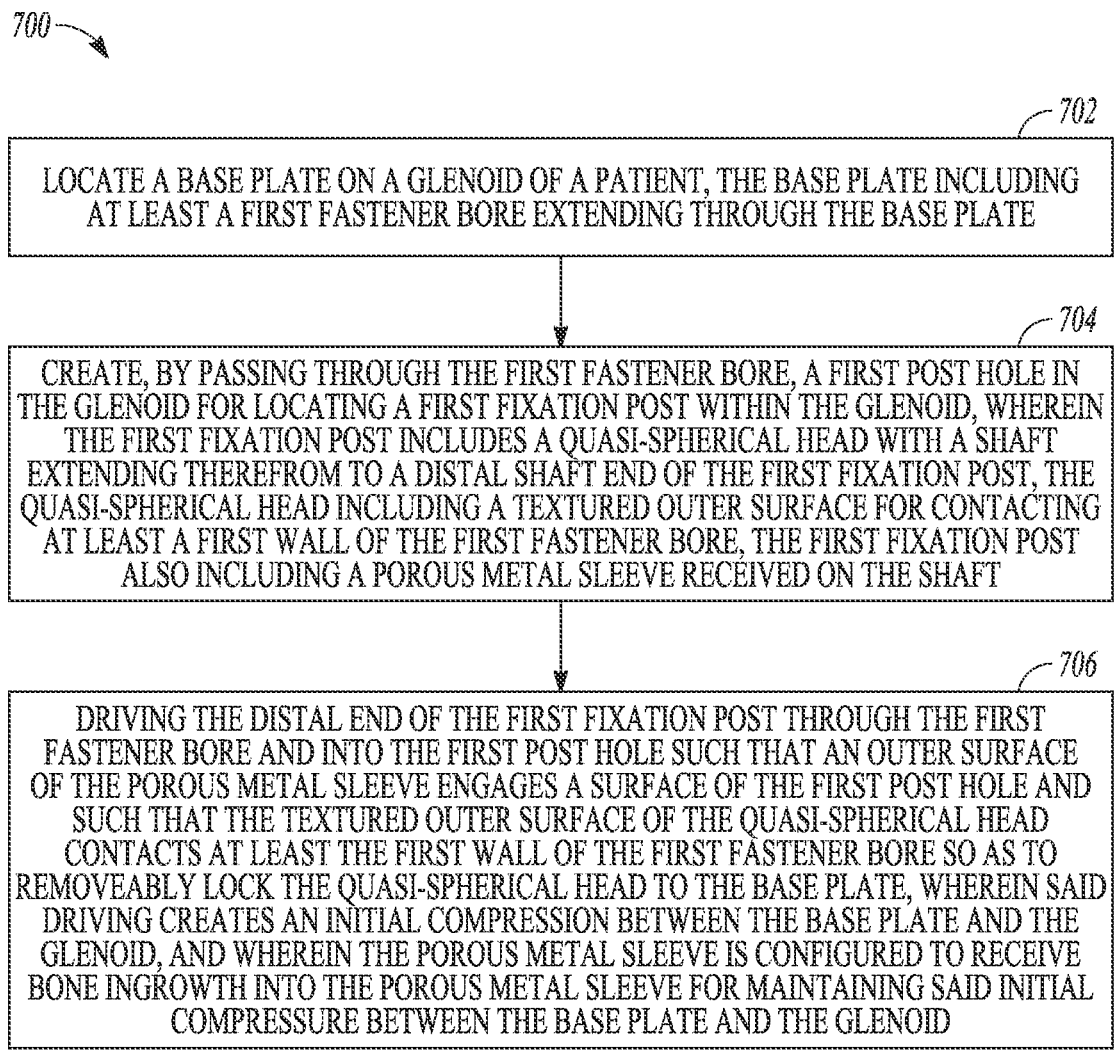
FIG. 7 shows a flowchart illustrating an example method for attaching an orthopedic device to a bone.

FIG. 7 shows a flowchart illustrating an exemplary method 700 for attaching an orthopedic device to a bone. At 702, a baseplate including at least a first fastener bore 656A extending through the baseplate 650, can be located on the glenoid of a patient. The base plate 650 can be located with respect to landmarks on the patient by, for example, aligning the first fastener bore 656A to the inferior scapular pillar or by aligning the first fastener bore 656A to the base of the coracoid.

At 704, a post hole, such as a first post hole, can be created in the glenoid to locate a first fixation post 670A within the glenoid. The first post hole can be positioned with respect to the baseplate 650 by passing through the first fastener bore 656A. The first fixation post 670A can include a core 110, such as a quasi-spherical head 112 with a shaft 114 extending from the quasi-spherical head 112 to a distal end 116 of the core 110, and a sleeve 120, such as a porous metal sleeve, received on the shaft 114 or around the shaft 114. The quasi-spherical head 112 can include a textured outer surface for contacting at least the first wall 659A of the first fastener bore 656A.

Creating a post hole through the first fastener bore 656A can include drilling a hole, such as a first post hole, in the glenoid. Drilling a hole can include using a drill bit to remove bone material from the first post hole, in combination with a drill tool that applies rotary motion to the drill bit. In an example, a drill bit can be attached to a drill tool that applies rotary motion, and the drill bit may optionally be located within the first fastener bore 656A, and the tool activated to impart rotary, motion to the drill bit to remove bone material from the first post hole. Drilling a hole can include using a chisel tool to remove bone material from the first post hole, such as with a tool that applies linear motion to the chisel tool. A chisel tool can include a tool with a cutting edge, such as at least one of a butt chisel, paring chisel, gouge, and punch. In an example, the chisel tool can be located in the first fastener bore 656A, such as against the patient bone, and an impulsive force applied to the chisel tool, such as with a hammer, such as a slap hammer, to remove bone material from the patient bone to create the first post hole.

Contacting at least the first wall 659A of the first fastener bore 656A with the textured outer surface of the quasi-spherical head 112 can include positioning at least a portion of the textured outer surface of the quasi-spherical head 112 against the wall 659 of a fastener bore 656, such as the first fastener bore 656A. The quasi-spherical head 112 can include a plurality of polygonal elements 78, and each polygonal element 78 can include at least one of an exterior face 87 and a vertex 88.

At 706, the first fixation post 670A can be driven through the first fastener bore 656A and into the first post hole, such that the exterior surface 128 of the sleeve 120, such as a porous metal sleeve, can engage a surface of the first post hole and the textured outer surface of the quasi-spherical head 112 can contact at least the first wall 659A of the first fastener bore 656A, so as to removably lock the quasi-spherical head 112 to the baseplate. Driving the first fixation post 670A into the first fastener bore can create an initial compression between the baseplate 650 and the glenoid. The sleeve 120 can be configured to receive bone ingrowth, such as into the porous metal sleeve, for maintaining said initial compression between the baseplate and the glenoid.

Driving the first fixation post 670A can include applying a force to the quasi-spherical head 112 of the first fixation post 670A. The force applied to the quasi-spherical head 112 can include at least one of an impact loading force applied with a hammer, such as a slap hammer, or a press loading force, such as applied with a pneumatic or hydraulic loading tool.

The exemplary method 700 can include creating a post hole, such as a second post hole, in the glenoid, to locate a second fixation post 6709 within the glenoid by passing through a second fastener bore 656B. The second fixation post 670B can be aligned with respect to the first fixation post. In an example, the second fixation post 670B can be aligned dependently upon the first fixation post 670A, such that the central axis of the first fixation post 670A and the central axis of the second fixation post 670B can be parallel or can form a predetermined angle with respect to each other. In an example, the second fixation post 670B can be aligned independently from the first fixation post 670A, such that the central axis of the first fixation post 670A and the central axis of the second fixation post 670B are not parallel, which may improve clinical outcomes due to increased bone capture, length, and inherent geometry.

The exemplary method 700 can include driving the second fixation post 670B through the second fastener bore 656B and into the second post hole, to enhance the initial compression between the baseplate and the glenoid.

VARIOUS NOTES

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel." "perpendicular," "round," or "square," are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed. Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An orthopedic assembly comprising:
   a baseplate including a fixation bore defining a bore axis, and
   a fixation post configured to attach the baseplate to a bone, the fixation post including:
      a quasi-spherical head positionable within the fixation bore in a plurality of different orientations relative to the bore axis, the quasi-spherical head including a textured outer surface;
      a shaft including a proximal end attached to the quasi-spherical head and a distal end opposite the proximal end; and
      a porous metal surface disposed on at least a portion of the shaft.

2. The orthopedic assembly of claim 1, wherein the shaft includes an anti-rotation feature.

3. The orthopedic assembly of claim 1, further comprising an anchor post extending from an inner bone-facing surface of the baseplate and configured to engage bone.

4. An orthopedic assembly comprising:
   a baseplate including a fixation bore; and
   a fixation post configured to extend at least partially through the fixation bore, the fixation post including:
      a quasi-spherical head positionable within the fixation bore in a plurality of different orientations, the quasi-spherical head including a textured outer surface;
      a shaft including a proximal end attached to the quasi-spherical head and a distal end opposite the proximal end, the shaft including an anti-rotation feature;
      a porous metal sleeve surrounding at least a portion of the shaft; and
      a cap attached to the distal end of the shaft to retain the porous metal sleeve on the shaft.

5. The orthopedic assembly of claim 4, wherein the shaft includes a bearing surface between the proximal and distal ends and the porous metal sleeve includes a central bore with a bore surface.

6. The orthopedic assembly of claim 5, wherein the bore surface substantially conforms with the bearing surface.

7. The orthopedic assembly of claim 6, wherein the quasi-spherical head and the shaft form a unitary core.

8. The orthopedic assembly of claim 6, wherein the porous metal sleeve includes a proximal sleeve surface in contact with the quasi-spherical head and a distal sleeve surface in contact with the cap.

9. The orthopedic assembly of claim 4, wherein the anti-rotation feature includes the shaft with a generally elliptical cross-section.

10. The orthopedic assembly of claim 4, wherein the cap includes a distal cap surface and wherein the distal cap surface is generally hemispherically shaped.

11. The orthopedic assembly of claim 4, wherein the cap includes a distal cap surface and wherein the distal cap surface is generally conically shaped.

12. The orthopedic assembly of claim 4, wherein the baseplate includes an outer surface and an inner bone-facing surface arranged opposite to the outer surface, and wherein the fixation bore extends through the baseplate from the outer surface to the inner bone-facing surface.

13. The orthopedic assembly of claim 12, wherein the fixation bore is defined by a bore wall, and wherein the bore wall is tapered between the outer surface and the inner bone-facing surface.

14. An orthopedic assembly comprising:
   a baseplate including an outer surface, an inner bone-facing surface, and a fixation bore extending through the baseplate from the outer surface to the inner bone-facing surface;
   an anchor post extending from the inner bone-facing surface of the baseplate and configured to engage bone; and
   a fixation post configured to extend at least partially through the fixation bore, the fixation post including:
      a quasi-spherical head positionable within the fixation bore in a plurality of different orientations, the quasi-spherical head including a textured outer surface;
      a shaft including a proximal end attached to the quasi-spherical head and a distal end opposite the proximal end; and a porous metal sleeve surrounding at least a portion of the shaft.

15. The orthopedic assembly of claim 14, wherein the anchor post is removable from the baseplate.

16. The orthopedic assembly of claim 14, further comprising a retaining cap attached to the distal end of the shaft.

17. The orthopedic assembly of claim 14, wherein the quasi-spherical head of the fixation post and the fixation bore of the baseplate are configured such that the fixation post is extendable at least partially through the fixation bore in a plurality of different orientations.

18. The orthopedic assembly of claim 14, wherein contact between the quasi-spherical head and a tapered wall of the fixation bore secures the baseplate to the fixation post.

19. The orthopedic assembly of claim 14, further comprising a spacer removably couplable to the outer surface of the baseplate.

\* \* \* \* \*